United States Patent [19]
Finel et al.

[11] Patent Number: 5,605,704
[45] Date of Patent: Feb. 25, 1997

[54] LIPOSOMES FOR DEPOSITION ON HAIR

[75] Inventors: Christophe M. Finel; Jonathan D. Hague; Euan S. Reid, all of Wirral, Great Britain

[73] Assignee: Chesebrough-Pond's USA Co., Division of Conopco, Inc., Greenwich, Conn.

[21] Appl. No.: 397,463

[22] Filed: Mar. 2, 1995

[30] Foreign Application Priority Data

Mar. 4, 1994 [EP] European Pat. Off. ............... 94301574

[51] Int. Cl.⁶ ................................................ A61K 9/127
[52] U.S. Cl. .................. 424/450; 424/70.1; 424/70.9; 424/70.27; 424/70.28; 514/880
[58] Field of Search ........................... 424/450, 70.1, 424/70.9, 70.27, 70.28; 514/800

[56] References Cited

U.S. PATENT DOCUMENTS

| | | | |
|---|---|---|---|
| 3,957,971 | 5/1976 | Oleniacz | 424/70 |
| 4,885,159 | 12/1989 | Miyake | 424/70 |
| 4,897,355 | 1/1990 | Eppstein | 435/240.2 |
| 4,964,874 | 10/1990 | Saphakkul | 8/429 |
| 5,229,104 | 7/1993 | Sottery | 424/59 |
| 5,288,423 | 2/1994 | Behan | 252/174.11 |
| 5,290,562 | 3/1994 | Meybeck | 424/450 |
| 5,328,628 | 7/1994 | Hart | 252/91 |
| 5,334,581 | 8/1994 | Behan | 514/2 |
| 5,362,494 | 11/1994 | Zysman et al. | 424/401 |

FOREIGN PATENT DOCUMENTS

| | | |
|---|---|---|
| 0373988 | 12/1988 | European Pat. Off. . |
| 267361 | 11/1992 | France . |

OTHER PUBLICATIONS

International Search Report PCT/EP 95/00716.

*Primary Examiner*—Gollamudi S. Kishore
*Attorney, Agent, or Firm*—Milton L. Honig

[57] ABSTRACT

A method is provided for treating hair with an active ingredient such as an anti-dandruff and/or sunscreen agent by delivery within a cationic liposomal dispersion. The dispersion is pre-prepared with inclusion of the active ingredient, and then incorporated into the final hair treatment composition.

4 Claims, No Drawings

LIPOSOMES FOR DEPOSITION ON HAIR

FIELD OF THE INVENTION

This invention concerns processes and compositions for the treatment of human hair. More particularly the invention concerns an improved system for the deposition of active ingredients on hair from hair treatment compositions.

BACKGROUND OF THE INVENTION AND PRIOR ART

When treating hair with rinse-off products incorporating surfactant soluble active ingredients, a considerable amount of the active ingredient will be rinsed away. Studies have shown that the level of retention in the case of a simple shampoo composition, where the active ingredient is solubilised in the surfactant micelles in the product, can be as low as 5%. Retention of these active ingredients from conditioning compositions is generally higher, probably because there is poorer solubilisation of the active ingredient in the conditioning base, but there is considerable scope for improvement, as this would provide better performance of the active ingredient and the option of reducing the level of expensive active ingredient in the product, with consequent cost saving.

It is an object of the present invention to provide an improved system for the deposition of active ingredients on hair.

BRIEF SUMMARY OF THE INVENTION

We have now found that cationic liposomes, ie. aqueous compartments enclosed by one or more lipid bilayers, can be formed which are storage-stable and possess an affinity for hair. When included in a hair treatment composition, these liposomes deposit on the hair, are not eliminated during rinsing and can enhance the deposition on the hair of active ingredients with which they are combined.

Accordingly, in a first aspect, the present invention provides a process for the deposition of an active ingredient on hair by cationic liposomes.

In a second aspect, the present invention provides a composition comprising cationic liposomes and an active ingredient, which when applied to hair will cause enhanced deposition of the active ingredient on the hair than previously achievable.

DETAILED DESCRIPTION OF THE INVENTION

A preferred process according to the invention comprises the following steps:

(a) forming a dispersion of cationic liposomes incorporating the active ingredient, (b) processing the dispersion into a hair treatment composition, and (c) treating the hair with the composition.

We have found that the dispersion of step(a) may be prepared by the simple addition of solid cholesterol, along with the active ingredient, to an aqueous solution of cationic surfactant. This induces the formation of liposomes, and the structures so generated may be easily visualised using conventional contrast microscopy techniques. The concentration of cationic surfactant in the liposomal dispersion is suitably from 2% to 10% by weight based on total weight, and the weight ratio of cholesterol to cationic surfactant is preferably 1:1.

Microscopy studies of liposomal dispersions prepared as above demonstrate at least partial encapsulation of the active ingredient in the liposomes. It is preferable to optimise such encapsulation to allow the best efficiency of deposition enhancement from the liposomal dispersions of the invention, although the exact mechanism by which this occurs is unclear. In general, it is less preferable to add the active ingredient at a later stage than addition of the liposomes, since this appears to be detrimental to encapsulation of the active ingredient by the liposomes.

However, in an alternative process according to the invention, a dispersion of cationic liposomes may be formed in situ in a hair treatment composition by the inclusion of liposomal components, typically cholesterol and cationic surfactant, during the processing stage. The active ingredient may then be incorporated into the composition after this stage.

In this alternative process, the concentration of cholesterol added during processing (by weight based on the total weight of the hair treatment composition) is suitably from 0.05 to 3%. e.g. 0.1 to 1% and the concentration of cationic surfactant added during processing is suitably from 0.15 to 5%, e.g. 0.5 to 2%, by weight based on total weight of the hair treatment composition.

Surprisingly, this also provides a favourable route to effective liposomal encapsulation of the active ingredient. It appears that in such a case, the whole of the compositional microstructure is altered so as to represent a favourable environment for active ingredient encapsulation.

The active ingredient is normally a water-insoluble or sparingly water-soluble substance, such as an oil which may take the form of a sunscreen. Among suitable sunscreens are, camphor derivatives, benzophenone compounds such as 4,4'-tetrahydroxy-benzophenone, sold commercially as Uvinul D50, and 2-hydroxy-4-methoxybenzophenone, sold commercially as Eusolex 4360, dibenzoyl methane derivatives such as t-butyl-4-methoxydibenzoylmethane, sold commercially as Parsol 1789, and isopropyldibenzoyl methane, sold commercially as Eusolex 8020. Preferred sunscreen materials are cinnamates, such as 2-ethylhexyl-p-methoxy cinnamate, sold commercially as Parsol MCX, 2-ethoxy ethyl-p-methoxy cinnamate, sold commercially as Giv-Tan F and isoamyl-p-methoxy cinnamate, sold commercially as Neo-Heliopan E1000.

The active ingredient may also be an antidandruff agent, such as zinc pyrithione, and other 1-hydroxy pyridones. A preferred antidandruff agent is the 1-hydroxy-2-pyridone derivative known as piroctone olamine, whose chemical name is 1-hydroxy-4-methyl-6-(2,4,4-trimethylpentyl)-2-pyridone monoethanolamine salt, and which is sold under the trade name OCTIPIROX by Hoechst AG.

Other suitable active ingredients are vitamin E and derivatives thereof, volatile oils and perfumes.

The active ingredient is normally present in a concentration of from 0.005% to 5%, preferably from 0.085% to 2% by weight based on the total weight of the hair treatment composition. The optimum concentration of active ingredient will depend on the precise chemical nature of the active ingredient. For a sunscreen, if the composition comprises less than 0.005% by weight of the sunscreen, little benefit will be obtained and if greater than 5% is present, it is unlikely that additional benefit will be obtained.

Examples of suitable cationic surfactants include: quaternary ammonium hydroxides, e.g. tetramethylammonium hydroxide, alkyltrimethylammonium hydroxides in which the alkyl group has from about 8 to 22 carbon atoms, for example octyltrimethylammonium hydroxide, dodecyltrimethylammonium hydroxide, hexadecyltrimethylammonium hydroxide, cetyltrimethylammonium hydroxide and behenyltrimethylammonium hydroxide, benzyltrimethylammonium hydroxide, octyldimethylbenzylammonium hydroxide, decyldimethylbenzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and their corresponding salts, e.g. halides Cetylpyridinium hydroxide or its corresponding salts, e.g. halide.

Preferred cationic surfactants are cetyl trimethylammonium chloride and cetyltrimethylammonium bromide, hereinafter referred to as C.T.A.C. and C.T.A.B. respectively.

Compositions according to the present invention may further comprise one or more optional ingredients which are normally found in hair treatment compositions. The compositions of the invention will preferably take the form of post-wash hair conditioning compositions or hair treatment masques, but may also take the form of conditioning shampoos or hair styling compositions or the like. One preferred optional component which may be included in the hair treatment compositions of the invention is a fatty alcohol or fatty acid, or derivative thereof, or a mixture of any of these, having a chain length of from about 8 to about 28 carbon atoms, more preferably from about 12 to about 18 carbon atoms. These materials may be predominantly linear or may be branched.

Such fatty material(s) may be present in the compositions of the invention in a total amount of from about 0.001 to 20% by weight, more preferably 0.01 to 10%, even more preferably 0.01 to 5% yet more preferably 0.1 to 1%. An especially preferred amount of the fatty material, if present, is up to about 0.5% by weight, since such amounts help to render the compositions smooth textured and non-lumpy.

Where it is desired to formulate a hair treatment composition of the invention which not only has conditioning properties but also has detergent properties, i.e. a shampoo, then one or more surfactants may be included, preferably selected from nonionic, amphoteric and zwitterionic surfactants.

Nonionic surfactants suitable for use in compositions of the invention include condensation products of aliphatic $C_8$–$C_{18}$) primary or secondary linear or branched chain alcohols or phenols with alkylene oxides, usually ethylene oxide, and generally having from 6 to 30 ethylene oxide groups.

Other suitable nonionics include mono- or di-alkyl alkanolamides. Examples include coco mono- or diethanolamide and coco mono-isopropanolamide. Further suitable nonionic surfactants are the alkyl polyglycosides (APG's). Typically, the APG is one which comprises an alkyl group connected (optionally via a bridging group) to a block of one or more glycosyl groups. Preferred APG's are described by the following formula:

RO- (G)$_n$

Wherein R is a branched or straight chain alkyl group which may be saturated or unsaturated and G is a saccharide group.

R may represent a mean alkyl chain length of from about $C_5$ to about $C_{20}$. Preferably, R represents a mean alkyl chain length of from about $C_8$ to about $C_{12}$. Most preferably the value of R lies between about 9.5 and about 10.5. G may be selected from $C_5$ or $C_6$ monosaccharide residues or mixtures of $C_5$ and $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; and APG225, APG300, APG350, APG550 and APG600 ex Henkel. Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

Further surfactants which may be suitable for use in shampoos in accordance with the invention include one or more anionic surfactants instead of or in addition to any of those surfactants mentioned above.

Suitable anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The surfactant(s) may be present in the hair treatment composition in a total amount of from about 1 to 70% by weight, preferably from 2 to 40% by weight, more preferably from 5 to 30% by weight.

As further optional components for inclusion in the compositions of the invention, in addition to water, the following may be mentioned: pH adjusting agents, viscosity modifiers, pearlescers, opacifiers, suspending agents, preservatives, colouring agents, dyes, proteins, herb and plant extracts, polyols and other moisturising and/or conditioning agents.

Embodiments of the present invention will now be further illustrated by reference to the following examples. All amounts given are in % by weight, unless otherwise stated.

EXAMPLES

Materials

Cholesterol was 95%, as supplied by Aldrich Chemical Co. CTAB was 99%, as supplied by Fluka AG. CTAC was obtained as a 50% solution (Arquad 16-50, obtained from AKZO). Octipirox and Parsol MCX were obtained from Hoescht and Givaudan-Roure respectively.

Methods

Liposome Preparation

CTAC was added to water at room temperature. Solid cholesterol was added, along with either Octipirox or Parsol MCX. The mixture was dispersed for three minutes with high shear at room temperature using a Silverson mixer. Liposome preparations were always 1:1 CTAC:Cholesterol by weight, and were between 2 and 10% CTAC.

Examples 1 to 3

Investigation of the affinity of liposomes for hair

A liposome solution was prepared as above using the following ingredients:

Cholesterol 0.125% (estimated total liposome concentration: 0.25%)
CTAC 0.125%
Demineralized water Procedure Hair switches of the same quality weighing about 1 g were selected, and each switch immersed separately in 15 ml of the prepared liposome solution. After removal of the switch, the concentration of each solution was investigated by measuring UV absorbance at 400 nm. The system was calibrated with two solutions having liposome concentration of 0.20% and 0.25%.

Results are given in Table 1:

TABLE 1

| Example | Switch immersion time | Final concentration of the solution |
| --- | --- | --- |
| 1 | 15 minutes | 0.246% |
| 2 | 2 hours | 0.233% |
| 3 | 16 hours | 0.231% |

Conclusion

If all of the components in the solution are assumed to be in the form of liposomes, the results indicate that liposomes are deposited on hair, as a result of the affinity between the liposomes and the hair.

Examples 4 and 5

Parsol MCX uptake by hair was examined:
from the liposomal dispersion alone, and from micellar CTAB solution.

Procedure

Hair switches were treated with 0.2 g conditioner/g hair, and 4×4 g switches were employed. Switches were extracted after rinsing with 100 ml of ethanol for 1 hour.

Parsol concentration in the ethanol solutions were determined using a calibration curve generated by several dilutions (in ethanol) of the initial liposome dispersion, or of Parsol MCX in ethanol. Absorbances were measured at a wavelength of 309 nm.

Table 2 displays retention results obtained from:
Comparative Example A: 4% CTAB, 0.3% Parsol MCX
Example 4: 4% CTAB, 4% Cholesterol, 0.3% Parsol MCX.
Comparative Example B: 2% CTAB, 0.15% Parsol MCX
Example 5: 2% CTAB, 2% Cholesterol, 0.15% Parsol MCX In Comparative Examples A and B, the Parsol MCX was shown by microscopy to be fully solubilised in the surfactant micelles. In Examples 4 and 5, the Parsol MCX was judged from microstructural studies to have been completely incorporated into the liposomal dispersion.

TABLE 2

| Example | Parsol Retained (ug/g Hair) | Efficiency of Parsol Retention |
| --- | --- | --- |
| 4 | 95 | 15.7 |
| Comparative Example A | 75 | 12.7 |
| 5 | 55 | 17.9 |
| Comparative Example B | 45 | 14.4 |

For each of the CTAB concentrations tested, addition of cholesterol, which induces liposomes in the system, allows a 25% increase in Parsol MCX retention.

Examples 6 to 8

Parsol MCX uptake was examined:
from fully formulated conditioners* with 10% post-processing additions of:
Comparative Example C: 2% Parsol MCX in distilled water,
Example 6: 7.5% CTAC, 7.5% Cholesterol, 2% Parsol MCX
Example 7: 10% CTAC, 10% Cholesterol, 2% Parsol MCX, and
Example 8: 4% CTAC, 4% Cholesterol, 0.85% Parsol The conditioner base to which the post-processing additions were made was made up from the following ingredients:

| Ingredient | % wt |
| --- | --- |
| CTAC | 0.7% |
| Cetearyl alcohol | 3.5% |
| paraffin | 1% |
| glyceryl stearate | 0.7% |
| butyl hydroxy toluene (BHT) | 0.05% |
| Bronopol (2-bromo-nitropropane-1,3-diol) | 0.01% |
| perfume | 0.2% |
| silk amino acids | 0.2% |
| demineralised water | 83.44% |

Procedure

Hair switches (1 g) were treated with 1 g of conditioner+ post-processing additive for 3 minutes, followed by a rinse of 1 minute. Switches were then extracted for 30 seconds with 10 ml of ethanol. Ethanolic extractions from the treated hair were diluted x15 with ethanol prior to measurement of absorbance.

Retention results are displayed in Table 3.

TABLE 3

| Example | Parsol Retained (ug/g Hair) | Efficiency of Parsol Retention (%) |
| --- | --- | --- |
| Comparative Example C | 800 | 4.1 |
| Example 6 | 1,150 | 5.6 |
| Example 7 | 1,550 | 7.7 |
| Example 8 | 800 | 9.6 |

The results demonstrate the advantage of processing Parsol MCX into the dispersion of CTAC/Cholesterol liposomes. Choosing a higher level of CTAC and cholesterol (Example 7) clearly allows a higher level of Parsol to be retained if the final concentration is 0.2% Parsol MCX. By solubilising a lower level of Parsol MCX (0.85%, giving a final concentration of 0.085%) into 4% CTAC, 4% Cholesterol, (Example 8), a retention level equivalent to that found in the control conditioner containing 0.2% Parsol MCX (Comparative Example C) can be achieved.

Examples 9 to 10

Effect of Method of Liposome Addition on Parsol MCX Uptake.

Parsol MCX retention was studied from the following systems (using a conditioner base made up as described under Examples 6 to 8):

Comparative Example D: Conditioner with a post-addition of 0.085% Parsol MCX.

Example 9: Conditioner with a 10% post-addition of a dispersion of 0.85% Parsol MCX, 4% Cholesterol, 4% CTAC.

Comparative Example E: Conditioner with a 10% post-addition of 4% Cholesterol, 4% CTAC, and with 0.085% Parsol MCX added separately.

Comparative Example F: Conditioner with 1.1% CTAC (extra) added in the fatty phase during processing, with 0.085% Parsol and 0.4% Cholesterol added post-processing.

Example 10: Conditioner with 1.1% CTAC, 0.4% Cholesterol added in the fatty phase during processing, and 0.2% Parsol MCX added post-processing.

Comparative Example G: Conditioner with 1.1% CTAC added in the fatty phase during processing, and 0.2% Parsol added post-processing. (No cholesterol).

The procedure followed was equivalent to that described above for Examples 6 to 8.

Results are detailed in Table 4:

TABLE 4

| Example | Parsol Retained (mg/g hair) | Efficiency of Parsol Retention (%) |
| --- | --- | --- |
| Comparative Example D | 375 | 4.1 |
| Example 9 | 800 | 9.1 |
| Comparative Example E | 625 | 7.5 |
| Comparative Example F | 400 | 5.2 |
| Example 10 | 1,825 | 9.1 |
| Comparative Example G | 1,300 | 6.4 |

The results suggest that addition of the pre-prepared liposomal components incorporating Parsol MCX after conditioner processing leads to the most effective Parsol MCX retention. However, adding a higher Parsol MCX concentration, after having processed the liposome components into the conditioner (Example 10), is also an effective route to high Parsol MCX retention. In this case, the inclusion of cholesterol at the processing stage seems to have a profound effect on the structure of the conditioner.

Example 11

Uptake of Octipirox from fully formulated conditioners

Octipirox retention was evaluated from the following conditioning formulations (the conditioner base being made up as described under Examples 6 to 8):

Comparative Example H: Conditioner with Octipirox (0.1%) added post-processing in the perfume phase.

Example 11: Conditioner with a 10% addition of 5% CTAC, 5% Cholesterol and 1% Octipirox.

Comparative Example I: Conditioner with a 10% addition of 5% CTAC, 5% Cholesterol, and with 0.1% Octipirox added separately in the perfume phase.

Procedure 1 g switches were treated with either 1 g or 0.2 g of conditioner+additive (1 minute application). After a 1 minute rinse, each switch was placed into a centrifuge tube and 10 ml of a solution comprising:

| | |
| --- | --- |
| 4% | Acetic acid (12%) |
| 2% | Iron (II) sulphate solution (0.17M, acidified with HCl) |
| 94% | Methanol | was added.

After 35 minutes (+/−30) seconds in contact with the switch, the mixture was centrifuged at 3500 rpm for 5 minutes. Octipirox content in the supernatant was estimated from absorbance measurement at 462 nm, using a previously determined calibration curve.

The results are shown in Table 5:

TABLE 5

| | Treatment with 1 g conditioner/g hair | | Treatment with 0.2 g conditioner/g hair | |
| --- | --- | --- | --- | --- |
| Example | Parsol Returned (ug/g hair) | Efficiency of Parsol Retention (%) | Example | Parsol retained (ug/g hair) | Efficiency of Parsol Retention (%) |
| Comparative Example H | 850 | 8.3 | Comparative Example H | 500 | 26.3 |
| Example 11 | 1,800 | 17.9 | Example 11 | 1,000 | 46.8 |
| Comparative Example I | 1,125 | 11.4 | Comparative Example I | 575 | 27.3 |

As was found with Parsol MCX, inclusion of the Octipirox into the liposomal dispersion offers a route to enhancement of retention of x2.

Conclusions

1) Addition of cholesterol to CTAC or CTAB solutions induces formation of coarse liposomes. The structures generated can easily be visualised using contrast microscopy techniques.

2) 1:1 CTAC: cholesterol liposomes are able to partially solubilise an active ingredient such as Parsol MCX or Octipirox.

3) When fully incorporated into a liposomal dispersion, Parsol MCX retention on hair can be increased by about 25% relative to retention from a micellar control.

4) When added as a component of a liposomal premix to a post-wash conditioner, up to 50% enhancement of the retention of both Parsol MCX and Octipirox may be achieved.

We claim:

1. A method for treating hair with an active ingredient comprising applying to the hair a hair treatment composition comprising a cationic liposomal dispersion incorporating the active ingredient, the cationic liposomal dispersion consisting essentially of:

(i) from 0.5 to 2% by weight of a cationic surfactant based on total weight of the hair treatment composition, the cationic surfactant being acetyl trimethylammonium salt;

(ii) from 0.1 to 1% by weight of cholesterol based on total weight of the hair treatment composition;

(iii) from 0.005 to 5% by weight of the active ingredient based on total weight of the hair treatment composition, the active ingredient being selected from the group consisting of sunscreen and anti-dandruff agents;

wherein the liposomal dispersion is pre-prepared, including the active ingredient therewithin, before combination into the hair treatment composition.

2. A method according claim 1 wherein the anti-dandruff agent is a 1-hydroxy pyridone.

3. The method according to claim 1 wherein the sunscreen agent is selected from the group consisting of 4,4'-tetrahydroxy-benzophenone, 2-hydroxy-4-methoxybenzophenone, t-butyl-4-methoxydibenzoylmethane, isopropyldibenzoyl methane, 2-ethylhexyl-p-methoxy cinnamate, 2-ethoxy ethyl-p-methoxy cinnamate and isoamyl-p-methoxy cinnamate.

4. The method according to claim 1 wherein the sunscreen agent is 2-ethylhexyl-p-methoxy cinnamate.

* * * * *

UNITED STATES PATENT AND TRADEMARK OFFICE
CERTIFICATE OF CORRECTION

PATENT NO. : 5,605,704
DATED : February 25, 1997
INVENTOR(S) : Finel et al.

It is certified that error appears in the above-indentified patent and that said Letters Patent is hereby corrected as shown below:

Column 8, line 64 change "acetyl" to -- a cetyl -- .

Signed and Sealed this

Twenty-ninth Day of April, 1997

Attest:

BRUCE LEHMAN

Attesting Officer

Commissioner of Patents and Trademarks